United States Patent [19]

Volkmann

[11] Patent Number: 4,921,972
[45] Date of Patent: May 1, 1990

[54] PROCESS FOR OPTICALLY ACTIVE 3-THIOLANYL SULFONATE ESTERS

[75] Inventor: Robert A. Volkmann, Mystic, Conn.

[73] Assignee: Pfizer Inc., New York, N.Y.

[21] Appl. No.: 378,888

[22] Filed: Jul. 12, 1989

Related U.S. Application Data

[60] Continuation-in-part of Ser. No. 353,374, May 17, 1989, abandoned, Division of Ser. No. 308,868, Feb. 9, 1989, Pat. No. 4,864,046.

[51] Int. Cl.$^5$ .................................. C07D 333/32
[52] U.S. Cl. ................................................ 549/66
[58] Field of Search ....................................... 549/66

[56] References Cited

U.S. PATENT DOCUMENTS 2,581,443  1/1952  Reynolds ........................ 260/247
2,726,162  12/1955 Allen ............................. 106/125
3,041,241  6/1962  Timmis ........................... 167/78

Primary Examiner—Alan Siegel
Attorney, Agent, or Firm—Peter C. Richardson; J. Trevor Lumb; Robert K. Blackwood

[57] ABSTRACT

Intermediates and a stepwise process for the conversion of an alkyl 4-chloro-3R-hydroxybutyrate to optically active compounds of the formula

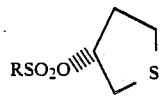

wherein R is $(C_1-C_3)$alkyl, phenyl or tolyl. The latter compounds are in turn useful as an intermediate in the preparation of penem antibiotic 5R,6S-6-(1R-hydroxyethyl)-2-(1R-oxo-3S-thiolanylthio)-2-penem-3-carboxylic acid and corresponding pharmaceutically acceptable salts and esters.

20 Claims, No Drawings

PROCESS FOR OPTICALLY ACTIVE 3-THIOLANYL SULFONATE ESTERS

CROSS REFERENCE TO RELATED APPLICATIONS

This application is a continuation-in-part of application Ser. No. 07/353,374 filed May 17, 1989, now abandoned; which is a division of application Ser. No. 07/308,868 filed Feb. 9, 1989, now U.S. Pat. No. 4,864,046.

BACKGROUND OF THE INVENTION

The present invention is directed to intermediates and a stepwise process for the conversion of a $(C_1-C_3)$alkyl 4-chloro-3R-hydroxybutyrate, of the formula (II) below, to optically active 3-thiolanyl sulfonate esters of the formula

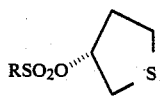
(I)

wherein R is $(C_1-C_3)$alkyl, phenyl or tolyl.

The compounds of formula (I) are particularly valuable intermediates in the preparation of certain penem antibiotics. Thus, antibacterial 5R,6S-6-(1R-hydroxyethyl)-2-(cis-1-oxo-3-thiolanylthio)-2-penem-3-carboxylic acid, which is a diastereomeric mixture of two compounds, was earlier disclosed as a valuable antibacterial substance by Hamanaka, U.S. Pat. No. 4,619,924; while Volkmann et al., in U.S. Pat. No. 4,739,047, have disclosed an alternative synthesis for that substance. More recently, the preferred diastereoisomer [5R,6S-6-(1R-hydroxyethyl)-2-(1R-oxo-3S-thiolanylthio)-2-penem-3-carboxylic acid] and a process therefor, have been identified and disclosed in my International Application No. PCT/US87/01114, designating inter alia the U.S. of America, published on Nov. 17, 1988 as WO-88/08845. Key to synthesis of this diastereoisomer is the optically active intermediate of the formula (I), earliest prepared by the following sequence:

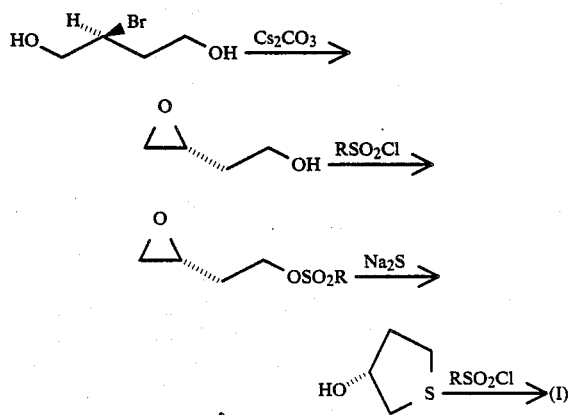

More recently, in commonly assigned, copending U.S. patent application, Ser. No. 07/183,102, filed Apr. 19, 1988, Urban describes a multistep synthesis of the compound of the formula (I) from D-methionine, as follows:

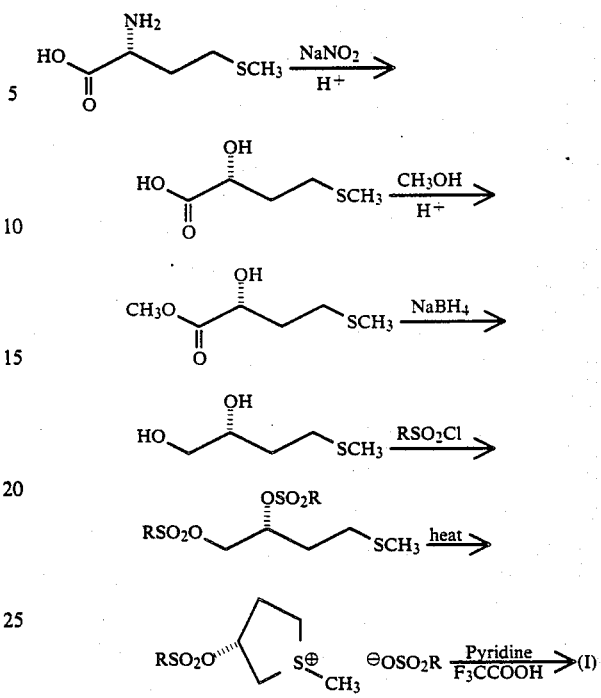

We have now discovered that the optically active compounds of the formula (I) are most conveniently and readily prepared by a three step process from ethyl 4-chloro-3R-hydroxybutyrate, an optically active compound now easily available in 97% yield by hydrogenation of ethyl 4-chloroacetoacetate over an optically active ruthenium catalyst according to the method of Kitamura, et al., Tetrahedron Letters, vol. 29, pp. 1555-1556, 1988.

The presently prepared thiolanyl sulfonate esters of the formula (I) are used in the synthesis of the above identified diastereomeric penem antibiotic according to methods which are available to the public in my published International patent application WO-88/08845, cited above, which also teaches the advantageous utility of this penem antibiotic.

SUMMARY OF THE INVENTION

The present invention is directed to a process for the preparation of an optically active compound of the formula

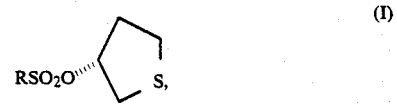
(I)

wherein R is $(C_1-C_3)$alkyl, phenyl or tolyl, which comprises the steps of:

(a) hydride reduction of an optically active ester of the formula

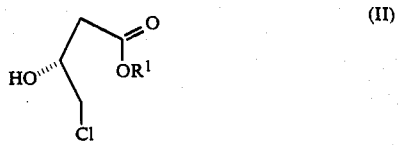
(II)

wherein R¹ is (C₁-C₃)alkyl with an amount of a hydride reducing agent capable of reducing an ester to an alcohol in a reaction-inert solvent to form an optically active diol of the formula

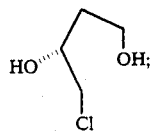

(III)

(b) reacting said diol in the same or another reaction-inert solvent with at least 2 molar equivalents of an activated form of a sulfonic acid of the formula RSO₂OH in the presence of at least 2 equivalents of a tertiary amine to form an optically active disulfonate of the formula

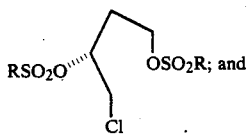

(IV)

(c) reacting said disulfonate with a sulfide salt in the same or another reaction-inert solvent to form the compound of the formula (I).

While conventional activation as a mixed anhydride, or with such reagents as dicyclohexylcarbodiimide or 1,1'-carbonyldiimidazole is generally satisfactory, the preferred activated form of the sulfonic acid in step (b) is the sulfonyl chloride, RSO₂Cl. The preferred values of R are methyl and p-tolyl. Alkali metal sulfides, particularly Na₂S, are the preferred sulfide salts in step (c). A variety of hydride reducing agents are generally useful in step (a). However, milder agents such as LiBH₄ are preferred, using amounts and solvents as defined below.

The present invention is also directed to the above compounds of the formula (III) and (IV), written in combined form as

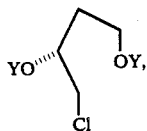

wherein Y is hydrogen or RSO₂— and R is (C₁-C₃)alkyl, phenyl or tolyl. When Y is RSO₂—, the preferred values of R are methyl and p-tolyl.

As employed above and elsewhere herein, the expression "reaction-inert solvent" refers to a solvent which does not interact with starting materials, reagents, intermediates or products in a manner which adversely affects the yield of the desired product.

DETAILED DESCRIPTION OF THE INVENTION

The present preparation of optically active thiolanyl sulfonate esters of the formula (I) from ethyl (R)-4-chloro-3-hydroxybutyrate (II) is readily carried out via the intermediates (R)-4-chlorobutane-1,3-diol (III) and disulfonate ester (IV), using the sequential steps of (a) hydride reduction, (b) bis-sulfonylation and (c) sulfide displacement/cyclization.

The hydride reduction step is carried out generally using at least two chemical equivalents of a conventional hydride reducing agent. For a review of such agents, see House, Modern Synthetic Reactions, 2nd ed., W. A. Benjamin Inc., Menlo Park, CA, pp. 45-105. The preferred agent in the present case is LiBH₄, in a reaction-inert solvent which will generally be aprotic (preferably a relatively polar ether such as tetrahydrofuran, dioxan or 1,2-dimethoxyethane). At least 2 chemical equivalents of LiBH₄ are used (i.e., 0.5 mol of LiBH₄/mol of ester substrate). Temperature is not particularly critical, but temperatures in the range of about 0°-30° C. are preferred.

The conversion of the diol to bis-sulfonate ester is also carried out in a conventional manner, preferably by combining the diol (II) with substantially 2 molar equivalents of a sulfonyl chloride of the formula RSO₂Cl (where R is as defined above) in a reaction-inert solvent (such as CH₂Cl₂ or tetrahydrofuran) in the presence of at least two molar equivalents of a tertiary amine such as triethylamine. For this generally exothermic reaction, temperatures below ambient (e.g., 10° to −30° C.) are preferred. The exotherm and temperature can be controlled in part by the rate of addition of the acid chloride. In a variation of this process, an excess of pyridine is used as both tertiary amine and solvent.

The sulfide displacement/cyclization step in which sulfide reacts to form the thiolane ring (by displacement of the 1-sulfonate ester group and the 4-chloro group) is carried out under conditions characteristic of nucleophilic displacement reactions in general, particularly with respect to the initial bimolecular displacement of either 4-chloro or the 1-sulfonate group, where the rate is favored by higher concentrations of the reactants and completeness of reaction is favored by use of an excess of one of the reagents (in this case usually the sulfide). However, the second stage cyclization is a zero order, intramolecular displacement, where the rate will be substantially independent of concentration, but where increasingly high concentrations will favor formation of undesired dimer, or even polymer. The preferred sulfide salts are alkali metal sulfides such as Na₂S). If desired an iodide salt such as tetrabutylammonium iodide can be used as catalyst. Solvent is not critical in this reaction, although acidic solvents are generally to be avoided so as to maintain the sulfide and intermediate mercaptide in more reactive anionic form. A preferred solvent system, which does not require iodide as catalyst, is aqueous acetonitrile. Temperature is not critical; it should be high enough that the reaction proceeds to completion within a reasonable period of time, but not so high as to lead to undue decomposition. Temperatures in the range of about 40°-100° C. are particularly well suited in the present case.

The following examples are given by way of illustration and are not to be construed as limitations of this invention, many variations of which are possible within the scope and spirit thereof.

EXAMPLE 1

(R)-4-Chlorobutane-1,3-diol

In flame dried glassware under nitrogen, methyl (R)-4-chloro-3-hydroxybutyrate (1.00 g, 6.55 mmol) was dissolved in 6.5 ml of dry tetrahydrofuran. The solution was cooled to 0° C. and a solution of lithium borohydride (178 mg, 8.19 mmol) in 4.1 ml of dry tetrahydrofuran was added by syringe over a 30 minute period, using 2 ml of tetrahydrofuran for rinse. The ice bath was removed and the solution stirred at 23° C. for 6 hours, then cooled to 0° C., quenched with 40 ml of methanol and acidified with 8 ml of saturated methanolic HCl. The mixture was stripped of solvent in vacuo and the residue treated with methanol and the reaction azeotroped (3×50 ml) to remove methyl borate and stripped to an oil (1.55 g). The latter was flash chromatographed on an 8.5 cm diameter×5 cm deep pad of silica gel gradiently eluted with CH$_2$Cl$_2$, 1:1 CH$_2$Cl$_2$:ethyl acetate and ethyl acetate to yield 0.67 g (82%) of title product as an oil; [alpha]$_D$= +24.5° (c=1.01, CH$_3$OH).

EXAMPLE 2

(R)-4-Chloro-3-(methanesulfonyloxy)butyl Methanesulfonate

In a 500 ml 3-neck flask under nitrogen, title product of preceding Example 5.0 g, 0.040 mol) was dissolved in 150 ml of CH$_2$Cl$_2$. The solution was cooled to −20° C. Triethylamine (8.12 g, 11.2 mls, 0.080 mol) and dimethylaminopyridine (0.48 g, 0.004 mol) were added followed by mesyl chloride (9.19 g, 6.21 ml, 0.080 mol). The solution was stirred at −20° to −15° C. for one hour and then poured over 1 liter of crushed ice and stirred for ten minutes. The separated aqueous layer was extracted with methylene chloride (1×300 ml). The combined organic layers were washed with 1N HCl (1×500 ml), saturated NaHCO$_3$ (1×500 ml) and brine (1×500 ml), dried over MgSO$_4$, and stripped in vacuo to afford 9.96 g (88%) of present title product; [alpha]$_D$= +32.74 (c=1.06, CHCl$_3$).

To prepare (R)-4-chloro-3-(p-toluenesulfonyloxy)-butyl p-toluenesulfonate, a molar equivalent of p-tolyl chloride is substituted for the mesyl chloride.

EXAMPLE 3

(R)-3-Thiolanyl Methanesulfonate

Title product of the preceding Example (3.5 g, 0.0125 mol) was dissolved in 60 ml of 1:6 H$_2$O:CH$_3$CN under N$_2$. Sodium sulfide nonahydrate (3.90 g, 0.050 mol) was added. After heating at 50° C. for 76 hours, the reaction mixture was diluted with 250 ml CH$_2$Cl$_2$, washed with H$_2$O (1×100 ml) and then brine (1×100 ml), dried over MgSO$_4$, and stripped in vacuo to yield present title product, which was by chromatography on silica gel using CH$_2$Cl$_2$ followed by 9:1 CH$_2$Cl$_2$:ethyl acetate as eluant to yield 1.30 g (57%) of present title product; [alpha]$_D$= +16.8° (c=3.0, CHCl$_3$).

By the same method the bis-p-tolyl ester of the preceding Example is converted to (R)-3-thiolanyl p-toluenesulfonate.

EXAMPLE 4

3R-(Methanesulfonyloxy)thiolane 1R-Oxide

By the method of Example 3 of published International patent application WO 88/08845, title product of the preceding Example (1.17 g, 6.42 mmol) and potassium peroxymonosulfate (Oxone; 2.21 g, 3.6 mmol) in 15 ml of acetone were converted to 0.96 g (75%) of present title product as a white solid; [alpha]$_D$= +2.04° (c=2.94, CHCl$_3$).

I claim:
1. A process for the preparation of an optically active compound of the formula

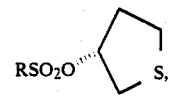

wherein R is (C$_1$-C$_3$)alkyl, phenyl or tolyl, which comprises the steps of:
(a) hydride reduction of an optically active ester of the formula

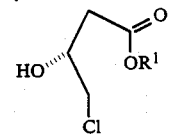

wherein R$^1$ is (C$_1$-C$_3$)alkyl with an amount of a hydride reducing agent capable of reducing an ester to an alcohol in a reaction-inert solvent to form an optically active diol of the formula

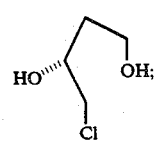

(b) reacting said diol in the same or another reaction-inert solvent with at least 2 molar equivalents of an activated form of a sulfonic acid of the formula RSO$_2$OH in the presence of at least 2 equivalents of a tertiary amine to form an optically active disulfonate of the formula

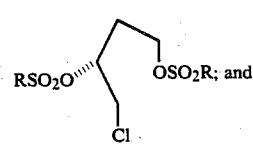

(c) reacting said disulfonate with a sulfide salt in the same or another reaction-inert solvent to form the compound of the formula (I).
2. A process of claim 1 wherein R is CH$_3$.
3. A process of claim 1 wherein R is p-tolyl.
4. A process of claim 1 wherein the hydride reducing agent is LiBH$_4$.
5. A process of claim 2 wherein the hydride reducing agent is LiBH$_4$.
6. A process of claim 4 wherein the solvent in step (a) is tetrahydrofuran.
7. A process of claim 5 wherein the solvent in step (a) is tetrahydrofuran.
8. A process of claim 1 wherein the activated form of the sulfonic acid is the acid chloride of the formula RSO$_2$Cl.
9. A process of claim 8 wherein R is CH$_3$.
10. A process of claim 8 wherein R is p-tolyl.
11. A process of claim 8 wherein the solvent in step (b) is CH$_2$Cl$_2$.
12. A process of claim 9 wherein the solvent in step (b) is CH$_2$Cl$_2$.
13. A process of claim 1 wherein the sulfide salt is an alkali metal sulfide.

14. A process of claim 13 wherein the sulfide salt is Na$_2$S.

15. A process of claim 14 wherein R is methyl.

16. A process of claim 14 wherein R is p-tolyl.

17. A process of claim 14 wherein the solvent is aqueous acetonitrile.

18. A process of claim 15 wherein the solvent is aqueous acetonitrile.

19. A process of claim 5 wherein the activated form of the sulfonic acid is methanesulfonyl chloride.

20. A process of claim 19 wherein the sulfide salt is Na$_2$S.

* * * * *